(12) United States Patent
Lee et al.

(10) Patent No.: US 10,383,800 B2
(45) Date of Patent: Aug. 20, 2019

(54) COSMETIC COMPOSITION

(71) Applicant: AMOREPACIFIC CORPORATION, Seoul (KR)

(72) Inventors: Su Jin Lee, Yongin-si (KR); Kyung Nam Kim, Yongin-si (KR); Yeong Jin Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 40 days.

(21) Appl. No.: 15/740,304

(22) PCT Filed: Jun. 23, 2016

(86) PCT No.: PCT/KR2016/006694
§ 371 (c)(1),
(2) Date: Dec. 27, 2017

(87) PCT Pub. No.: WO2017/003131
PCT Pub. Date: Jan. 5, 2017

(65) Prior Publication Data
US 2018/0177694 A1   Jun. 28, 2018

(30) Foreign Application Priority Data
Jun. 30, 2015 (KR) .......................... 10-2015-0093054

(51) Int. Cl.
*A61K 8/02* (2006.01)
*A61K 8/29* (2006.01)
*A61Q 1/02* (2006.01)
*A61Q 19/00* (2006.01)

(52) U.S. Cl.
CPC ................ *A61K 8/29* (2013.01); *A61K 8/025* (2013.01); *A61K 8/0245* (2013.01); *A61Q 1/02* (2013.01); *A61K 2800/20* (2013.01); *A61K 2800/412* (2013.01); *A61K 2800/5922* (2013.01); *A61Q 19/00* (2013.01)

(58) Field of Classification Search
None
See application file for complete search history.

(56) References Cited

U.S. PATENT DOCUMENTS

2014/0112965 A1*   4/2014   Nakamura ............. B82Y 30/00
424/401

FOREIGN PATENT DOCUMENTS

| JP | 2005519970 A | 7/2005 |
|----|--------------|--------|
| KR | 890004680 B1 | 11/1989 |
| KR | 20090032629 A | 4/2009 |
| KR | 20100055063 A | 5/2010 |
| KR | 20110043125 A | 4/2011 |
| KR | 20130011584 A | 1/2013 |

OTHER PUBLICATIONS

ISA Korean Intellectual Property Office, International Search Report Issued in Application No. PCT/KR2016/006694, Sep. 20, 2016, WIPO, 4 pages.

* cited by examiner

*Primary Examiner* — Gina C Justice
(74) *Attorney, Agent, or Firm* — McCoy Russell LLP

(57) ABSTRACT

Provided is a cosmetic composition including irregular titanium dioxide, and any one or two selected from the group consisting of spherical titanium dioxide having an average particle diameter of 200-400 nm and needle-shaped titanium dioxide having an average aspect ratio of length/thickness of 10-15.

5 Claims, 2 Drawing Sheets

COSMETIC COMPOSITION

CROSS-REFERENCE TO RELATED APPLICATIONS

The present application is a U.S. National Phase of International Patent Application Serial No. PCT/KR2016/006694 entitled "COSMETIC COMPOSITION," filed on Jun. 23, 2016. International Patent Application Serial No. PCT/KR2016/006694 claims priority to Korean Patent Application No. 10-2015-0093054, filed on Jun. 30, 2015. The entire contents of each of the above-cited applications are hereby incorporated by reference in their entirety for all purposes.

TECHNICAL FIELD

The following disclosure relates to a cosmetic composition, and more particularly, to a cosmetic composition having excellent coverability, spreadability, and sustainability.

BACKGROUND

Cosmetics are largely classified into base makeup cosmetics which are applied to an entire face, and point makeup cosmetics which are applied to only a small portion of a face.

Among these, the base makeup cosmetics are often used for the main purpose of covering or concealing skin blemishes such as facial freckles, wrinkles and spots to represent clean and white skin.

Usually, as a method for covering skin blemishes, a cosmetic composition was prepared by increasing a titanium dioxide content having excellent concealment power, however, as the titanium dioxide content was increased, the composition had reduced spreadability, for example, it became stiff, and more agglomerated.

On the contrary, in the case that the titanium dioxide content was decreased, the spreadability was improved, but concealment power was significantly lowered, thereby revealing skin blemishes as they are, or the cosmetics were rapidly disappeared to lower sustainability. Further, in order to cover the skin blemishes, the formulation should be applied thickly when putting on makeup, which does not fit the trend of thin makeup, and thus, is less competitive.

That is, when one effect was improved, the other effects were reduced.

Thus, there is a current need to develop a cosmetic composition having excellent coverability, spreadability, and sustainability, and capable of being applied thinly.

As a similar related art document improving the spreadability and the like, Korean Patent Laid-Open Publication No. 10-2010-0055063 has been suggested.

RELATED ART DOCUMENT

Patent Document

Korean Patent Laid-Open Publication No. 10-2010-0055063 (May 26, 2010)

SUMMARY

An embodiment of the present invention is directed to providing a cosmetic composition having excellent coverability, spreadability, and sustainability.

In one general aspect, a cosmetic composition includes irregular titanium dioxide, and any one or two selected from the group consisting of spherical titanium dioxide having an average particle diameter of 200-400 nm, and needle-shaped titanium dioxide having an average aspect ratio of length/thickness of 10-15.

Other features and aspects will be apparent from the following detailed description, the drawings, and the claims.

DETAILED DESCRIPTION OF EMBODIMENTS

Figure 1:
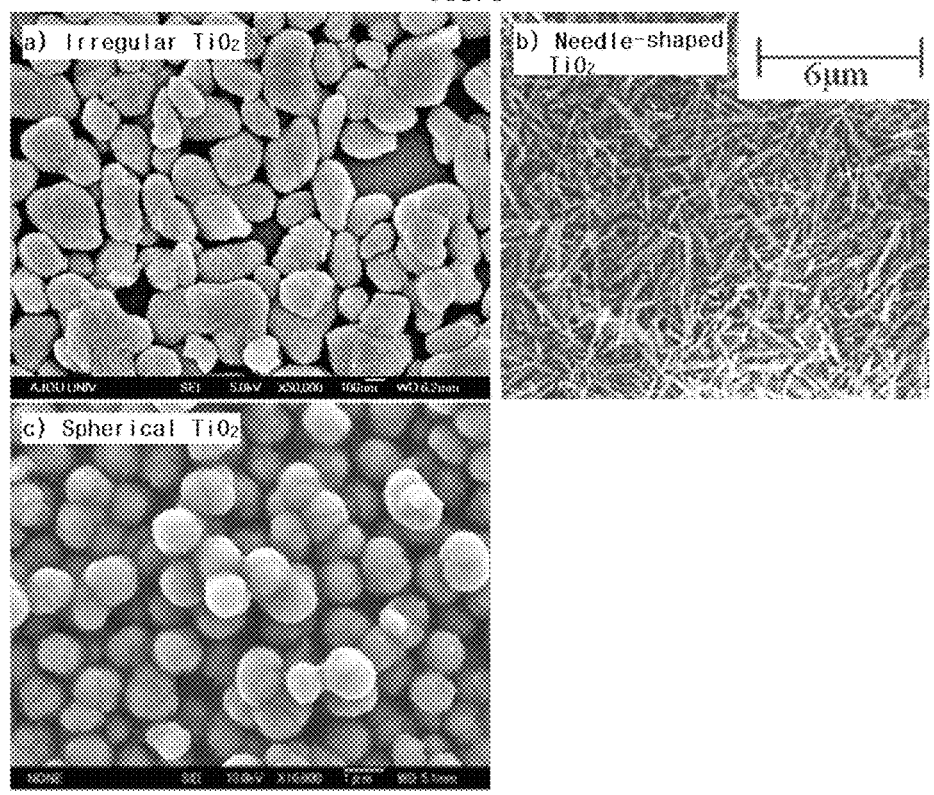
FIG. 1 is scanning electron microscopic (SEM) images of a) irregular titanium dioxide, b) needle-shaped titanium dioxide and c) spherical titanium dioxide, according to an exemplary embodiment of the present invention.
Figure 2:
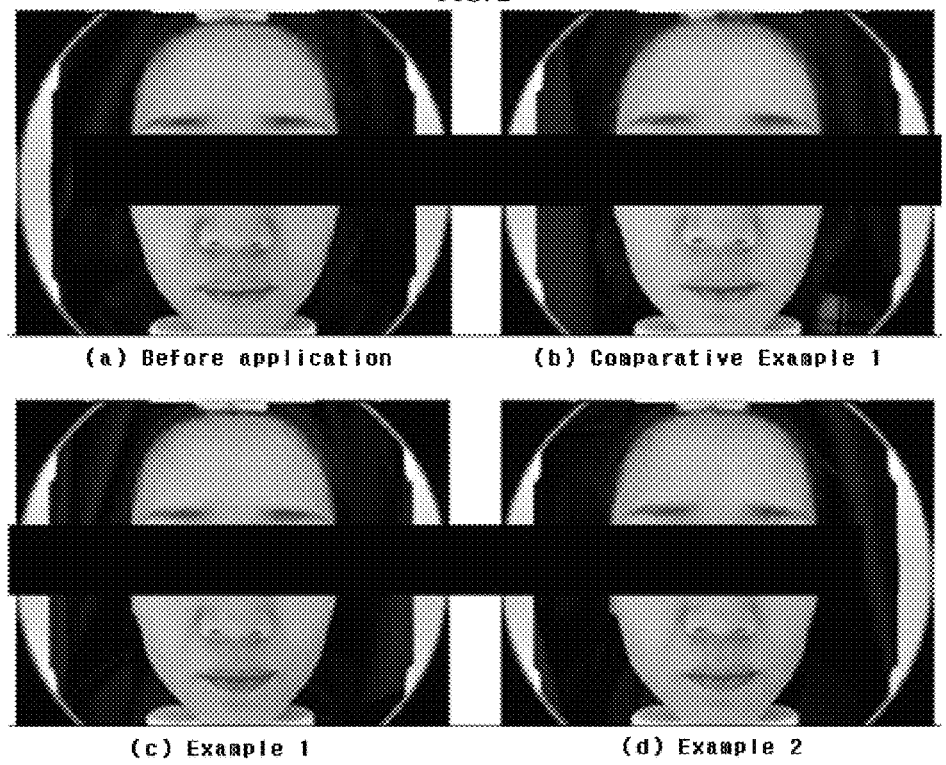
FIG. 2 is photographic images of coverability measurement, which are images a) before applying cosmetic compositions, b) after applying the cosmetic composition according to Comparative Example 1, c) after applying the cosmetic composition according to Example 1, and d) after applying the cosmetic composition according to Example 2.

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

In the conventional cosmetic composition, as one way to cover skin blemishes such as rashes, spots and freckles, a high content of titanium dioxide has been added thereto. However, in this case, though coverability was improved, as the cosmetic composition became stiff, spreadability and sustainability were deteriorated when applied to the skin, and feeling of use was deteriorated, for example, the cosmetics agglomerated.

As a solution of these problems, the present inventors intended to provide a cosmetic composition having excellent concealment, that is, excellent coverability, spreadability, and sustainability, without excessively increasing a titanium dioxide content, by mixing and adding titanium dioxides having different shapes.

Specifically, a cosmetic composition including irregular titanium dioxide, and any one or two selected from the group consisting of spherical titanium dioxide having an average particle diameter of 200-400 nm, and needle-shaped titanium dioxide having an average aspect ratio of length/thickness of 10-15 is provided.

When only irregular titanium dioxide is used, the particles agglomerate, and thus, a spreading property, that is, dispersibility is deteriorated when applying a cosmetic composition to the skin, particularly the face, and the skin tone may be nonuniform, and the composition is stiff, so that spreadability and sustainability are not good. However, when any one or two titanium dioxides selected from the group consisting of spherical titanium dioxide and needle-shaped titanium dioxide are mixed and added thereto, the agglomerates of irregular titanium dioxide are broken into primary particles again by spherical and needle-shaped titanium dioxide, and thus, agglomeration is significantly reduced to improve the spreading property, and as titanium dioxide is evenly distributed, the skin tone may become uniform. Particularly, as titanium dioxides having different shapes, but the same component are used together, coverability by titanium dioxide will not be deteriorated. However, when extender pigments having different shape and component, for example, silica, a polymer or the like are used, a concealment effect may be deteriorated to significantly lower the coverability. That is, the cosmetic composition according to the present invention may improve spreadability and sustainability, while maintaining coverability at high level, by mixing and adding titanium dioxide of any one or two selected from the group consisting of spherical titanium dioxide and needle-shaped titanium dioxide to irregular titanium dioxide.

The irregular titanium dioxide according to an exemplary embodiment of the present invention may be pelletized-type titanium dioxide without a certain shape, and any titanium dioxide may be used without particular limitation, as long as it is commonly used in the art. The average particle diameter thereof is not particularly limited, as long as the particles have the size to reflect light in a visible region, however, the average particle diameter may be for example, 150-450 nm, and more preferably, 250-350 nm is effective for excellent coverability.

It is preferred that the spherical titanium dioxide according to an exemplary embodiment of the present invention may have, as mentioned above, an average particle diameter of 200-400 nm, and the particles in such a range may reflect light in a visible region, thereby improving spreadability and sustainability, while maintaining excellent coverability. More preferably, spherical titanium dioxide having an average particle diameter of 250-350 nm may be preferred for more effective skin blemish concealment.

It is preferred that the needle-shaped titanium dioxide according to an exemplary embodiment of the present invention has an average aspect ratio of length/thickness of 10-15, as mentioned above, and in this case, the thickness may be 100-200 nm, but not limited thereto. The needle-shaped titanium dioxide in such a range may improve spreadability and sustainability, while maintaining excellent coverability. More preferably, the needle-shaped titanium dioxide having an average aspect ratio of 12-13 may be preferred for more effective skin blemish concealment.

Further, it may be important to adjust the content in the composition, in order to have excellent coverability and spreadability. The composition according to an exemplary embodiment of the present invention may satisfy the following Equation 1:

$$0.05 \leq [(T_S+T_N)/(T_I+T_S+T_N)] \leq 0.5 \quad \text{[Equation 1]}$$

wherein $T_I$ is % by weight of irregular titanium dioxide, based on a total weight of the composition; $T_S$ is % by weight of spherical titanium dioxide, based on the total weight of the composition; $T_N$ is % by weight of needle-shaped titanium dioxide, based on the total weight of the composition; and $T_S$ or $T_N$ may be 0% by weight. By way of example, $T_I+T_S+T_N$ may be 3-20, but not limited thereto.

As such, titanium dioxides having different shapes may be mixed and added in a ratio satisfying Equation 1 to the cosmetic composition, thereby effectively breaking the combined agglomerates of irregular titanium dioxide, and thus, the spreading property of irregular titanium dioxide may be improved, thereby more effectively covering skin blemishes, and allowing the skin tone to be uniform.

More preferably, $T_I+T_S+T_N$ may be 5-15, and $[(T_S+T_N)/(T_I+T_S+T_N)]$ may be 0.1-0.3. Titanium dioxides having different shapes may be mixed so that the above two conditions are satisfied, thereby more improving coverability and spreadability.

As described above, the cosmetic composition according to the present invention may have excellent coverability, spreadability, and sustainability by using titanium dioxide of any one or two selected from the group consisting of spherical titanium dioxide and needle-shaped titanium dioxide, together with irregular titanium dioxide.

Specifically, the composition according to an exemplary embodiment of the present invention may have the coverability (C) satisfying the following equation.

$$[(I-I_0)/I_0] \times 100 \geq 9.5 \quad \text{[Equation 2]}$$

wherein $I_0$ is skin brightness before makeup; and I is skin brightness after makeup. Here, the skin brightness may be measured using an image analysis program (Image Pro+), after photographing the image of the front face (Visia CR). The higher the coverability (C) value is, the brighter the skin tone is, and skin blemishes are concealed, thereby showing uniform skin tone.

Further, the composition according to an exemplary embodiment of the present invention may have the sustainability (S) satisfying the following Equation 3.

$$[(C_0-C_4)/C_0] \times 100 \geq 80 \quad \text{[Equation 3]}$$

wherein $C_0$ is coverability right after makeup, and $C_4$ is coverability after 4 hours from makeup. That is, as 80% or more of the coverability is maintained even after 4 hours, which is an indicator confirming that the makeup effect is maintained after a certain period of time, it is appreciated that the cosmetic composition of the present invention has excellent sustainability.

Besides, the cosmetic composition according to an exemplary embodiment of the present invention may further include oily materials, aqueous materials, surfactants, colorants, perfumes, preservatives, disinfectants, pearl agents, and the like, which are commonly used in the art, within a range not deteriorating the effect of the composition.

As such, the cosmetic composition having excellent coverability, spreadability, and sustainability may be used for a makeup base, foundation, BB cream, a concealer or the like, but not limited thereto.

Hereinafter, the cosmetic composition according to the present invention will be described in more detail by the following Examples. However, the following Examples are only a reference for describing the present invention in detail, and the present invention is not limited thereto, and may be implemented in various forms.

In addition, unless otherwise defined, all technical and scientific terms have the same meaning as commonly understood by a person skilled in the art to which the present invention pertains. The terms used in the description herein are only for effectively describing a certain example, and not intended to limit the present invention.

Further, the drawings to be provided below are provided by way of example so that the idea of the present invention can be sufficiently transferred to a person skilled in the art. Therefore, the present invention is not limited to the drawings provided below but may be modified in many different forms. In addition, the drawings suggested below will be exaggerated in order to clear the spirit and scope of the present invention.

Further, the singular form used in the specification and attached claims may also include the plural forms, unless otherwise stated in the context.

Further, unless otherwise stated in the specification, the unit of added materials may be % by weight (wt %).

The physical properties of the cosmetic composition prepared by the following Examples and Comparative Examples were measured as follows:

(Coverability)

Coverability, $C(\%)=[(I-I_0)/I_0] \times 100$

After photographing the image of a front face (Visia CR), an image analysis program (Image Pro+) was used to measure the skin brightness ($I_0$) before makeup, and the skin brightness (I) after makeup, and then the coverability was calculated using the above equation.

(Spreadability)

Figure 3:
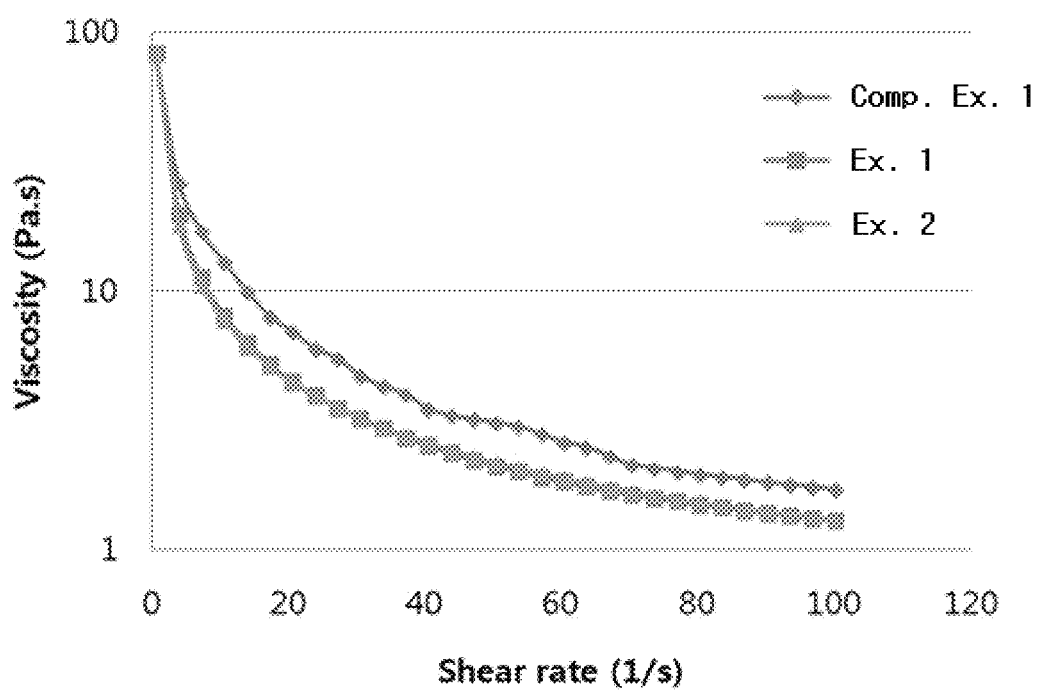
FIG. 3 is a shear rate/viscosity graph of the cosmetic compositions according to Examples 1 and 2, and Comparative Example 2, measured by a rheometer (Rheometer Rar 2000, TA Instrument).

Rheometer Rar 2000 (TA instrument) was used (cosmetics were loaded to the Rheometer Plate, set at 25° C., using a 40 mm diameter plate, gap: set at 31) to calculate the absolute value of the initial slope corresponding to 0-20 shear rates in the shear rate/viscosity graph as shown in FIG. 3, thereby comparing the spreadability.

In addition, sensory evaluation was requested of 10 panels of the average age of 32 years, who compared the spreadability using an evaluation form of one point scale unit out of 10 points, thereby calculating the average value.

(Sustainability)

Sustainability, $S(\%)=[(C_0-C_4)/C_0] \times 100$

The above coverability measurement method was used to measure the coverability ($C_0$) right after makeup, and the coverability ($C_4$) after 4 hours from makeup, and then the sustainability was calculated by the above equation.

Example 1

Irregular titanium dioxide having an average particle diameter of 300 nm, and needle-shaped titanium dioxide of length 1.7 μm/thickness 0.13 μm having an average aspect ratio of 13.1 were prepared, respectively.

The contents (wt %) in Table 1 were weighted for the corresponding prepared powder, and premixed with a dry mixer, and then a foundation was prepared according to a common preparation method of oil-in-water emulsion-type foundation.

Examples 2 and 3, and Comparative Examples 1 to 3

The entire process was carried out identically to Example 1, except for that the components and contents in the following Table 1 were used, and the physical properties thereof are shown in Table 2. However, spherical titanium dioxide, spherical silica and spherical polymethyl methacrylate (PMMA) had an average particle diameter of 300 nm, and PMMA had a weight average molecular weight of 500,000.

TABLE 1

|  | Irregular $TiO_2$ | Needle-shaped $TiO_2$ | Spherical $TiO_2$ | Spherical silica | Spherical PMMA |
|---|---|---|---|---|---|
| Example 1 | 10 | 2.5 | — | — | — |
| Example 2 | 10 | — | 2.5 | — | — |
| Example 3 | 10 | 1.25 | 1.25 | — | — |
| Comparative Example 1 | 12.5 | — | — | — | — |
| Comparative Example 2 | 10 | — | — | 2.5 | — |
| Comparative Example 3 | 10 | — | — | — | 2.5 |

TABLE 2

|  | Coverability (%) | Spreadability Initial slope | Spreadability Panel evaluation score | Sustainability (%) |
|---|---|---|---|---|
| Example 1 | 10.3 | 4 | 6.8 | 82 |
| Example 2 | 10.7 | 4.1 | 7 | 81 |
| Example 3 | 10.5 | 4.1 | 7 | 82 |
| Comparative Example 1 | 11.6 | 3.6 | 4 | 72 |
| Comparative Example 2 | 7.8 | 4 | 6.3 | 75 |
| Comparative Example 3 | 8.2 | 4 | 6.5 | 76 |

As shown in the above Tables 1 and 2, excellent coverability and spreadability, and better sustainability may be confirmed from Examples 1 to 3 in which any one or two titanium dioxides selected from the group consisting of spherical titanium dioxide and needle-shaped titanium dioxide were mixed and added to irregular titanium dioxide.

In contrast, excellent coverability, but significantly deteriorated spreadability and sustainability are confirmed from Comparative Example 1 in which only irregular titanium dioxide was used. Also, good spreadability, but significantly deteriorated coverability, and somewhat deteriorated sustainability are confirmed from Comparative Examples 2 and 3 in which extender pigments having different components and shapes were added.

That is, titanium dioxides having different shapes may be mixed and added to irregular titanium dioxide, thereby improving spreadability and sustainability, while maintaining high coverability.

Comparative Examples 4 to 6

The entire process was carried out identically to Example 1, except for that needle-shaped titanium dioxide of length 5.2 μm/thickness 0.27 μm having an average aspect ratio of 19.3 was used in Comparative Example 4, spherical titanium dioxide having an average particle diameter of 500 nm was used in Comparative Example 5, and spherical titanium dioxide having an average particle diameter of 1000 nm was used in Comparative Example 6, and the physical properties thereof are shown in Table 3.

TABLE 3

| | Coverability (%) | Spreadability | | Sustainability (%) |
| --- | --- | --- | --- | --- |
| | | Initial slope | Panel evaluation score | |
| Comparative Example 4 | 9.4 | 4.1 | 6.6 | 72 |
| Comparative Example 5 | 9.8 | 4.2 | 6.8 | 75 |
| Comparative Example 6 | 9.5 | 4.2 | 6.5 | 72 |

In Comparative Examples 4, 5 and 6, titanium dioxides having the same content and shape, but different average sizes such as aspect ratio or particle diameter were added, respectively, and as shown in Table 3, in the case that the titanium dioxides had too large size, somewhat reduced coverability and spreadability, and significantly lowered sustainability, as compared with Example 1 or 2, may be confirmed. This may be due to increased average size of titanium dioxide, which deteriorates the effect of reflecting visible light, and thus, lowers concealment power.

Examples 4 to 7

The entire process was carried out identically to Example 1, except for that the components and contents (wt %) of the following Table 4 were used, and the physical properties thereof are shown in Table 5.

TABLE 4

| | Irregular TiO$_2$ | Needle-shaped TiO$_2$ | Spherical TiO$_2$ |
| --- | --- | --- | --- |
| Example 4 | 11.25 | 1.25 | — |
| Example 5 | 8.75 | 3.75 | — |
| Example 6 | 11.25 | — | 1.25 |
| Example 7 | 8.75 | — | 3.75 |

TABLE 5

| | Coverability (%) | Spreadability | | Sustainability (%) |
| --- | --- | --- | --- | --- |
| | | Initial slope | Panel evaluation score | |
| Example 4 | 11.0 | 3.8 | 5.2 | 80 |
| Example 5 | 9.5 | 4.6 | 8.1 | 85 |
| Example 6 | 11.3 | 3.9 | 5.4 | 80 |
| Example 7 | 9.9 | 4.9 | 8.4 | 82 |

As shown in the above Tables 4 and 5, it may be confirmed that when the entire content of titanium dioxide is identical, the coverability, spreadability, and sustainability are varied with the mixed ratio of spherical or needle-shaped titanium dioxide, and especially in the case of Examples 1 and 2 where the weight ratio of irregular titanium dioxide: needle-shaped or spherical titanium dioxide was 4:1, it may be confirmed that the coverability was maintained at high level, while the spreadability and sustainability were also high.

The cosmetic composition according to the present invention may have excellent coverability, spreadability, and sustainability by mixing and adding titanium dioxide of any one or two selected from the group consisting of spherical titanium dioxide and needle-shaped titanium dioxide to irregular titanium dioxide.

What is claimed is:

1. A cosmetic composition comprising:
   irregular titanium dioxide, and
   any one or two selected from the group consisting of spherical titanium dioxide having an average particle diameter of 200-400 nm, and needle-shaped titanium dioxide having an average aspect ratio of length/thickness of 10-15.

2. The cosmetic composition of claim 1, wherein it satisfies following Equation 1:

$$0.05 \leq [(T_S + T_N)/(T_I + T_S + T_N)] \leq 0.5 \qquad \text{[Equation 1]}$$

wherein $T_I$ is % by weight of irregular titanium dioxide, based on a total weight of the composition;

$T_S$ is % by weight of spherical titanium dioxide, based on the total weight of the composition; and $T_N$ is % by weight of needle-shaped titanium dioxide, based on the total weight of the composition;

with a proviso that $T_S$ or $T_N$ may be 0% by weight.

3. The cosmetic composition of claim 1, wherein it has coverability (C) satisfying following Equation 2:

$$[(I - I_0)/I_0] \times 100 \geq 9.5 \qquad \text{[Equation 2]}$$

wherein $I_0$ is skin brightness before makeup; and

I is skin brightness after makeup.

4. The cosmetic composition of claim 3, wherein it has sustainability (S) satisfying following Equation 3:

$$[(C_0 - C_4)/C_0] \times 100 \geq 80 \qquad \text{[Equation 3]}$$

wherein $C_0$ is coverability right after makeup; and $C_4$ is coverability after 4 hours from makeup.

5. The cosmetic composition of claim 1, wherein it is for a makeup base, foundation, BB cream, or a concealer.

* * * * *